United States Patent
Badat (10) Patent No.: US 12,121,361 B2
(45) Date of Patent: Oct. 22, 2024

(54) APPARATUS AND METHOD OF USE TO MONITOR CHANGES IN BREAST MILK VOLUME

(71) Applicant: Haroon Iqbal Badat, Houston, TX (US)

(72) Inventor: Haroon Iqbal Badat, Houston, TX (US)

( * ) Notice: Subject to any disclaimer, the term of this patent is extended or adjusted under 35 U.S.C. 154(b) by 136 days.

(21) Appl. No.: 17/590,827

(22) Filed: Feb. 2, 2022

(65) Prior Publication Data
US 2022/0249011 A1 Aug. 11, 2022

Related U.S. Application Data

(60) Provisional application No. 63/147,404, filed on Feb. 9, 2021.

(51) Int. Cl.
| | | |
|---|---|---|
| *A41C 3/04* | (2006.01) | |
| *A61B 5/00* | (2006.01) | |
| *G01G 19/44* | (2006.01) | |
| *G01G 19/52* | (2006.01) | |
| *G16H 40/63* | (2018.01) | |

(52) U.S. Cl.
CPC ............. *A61B 5/4288* (2013.01); *A41C 3/04* (2013.01); *A61B 5/6804* (2013.01); *G01G 19/44* (2013.01); *G01G 19/52* (2013.01); *G16H 40/63* (2018.01)

(58) Field of Classification Search
CPC ......... A41C 3/04; G01G 19/44; A61B 5/6804
USPC ............................................... 450/36
See application file for complete search history.

(56) References Cited

U.S. PATENT DOCUMENTS

| | | | |
|---|---|---|---|
| 7,621,797 B1* | 11/2009 | Hershkovich | A41C 3/04 604/74 |
| 10,463,082 B2* | 11/2019 | Boele | A41C 3/0035 |
| 11,617,399 B2* | 4/2023 | Akerson | A41C 3/04 450/36 |
| 2008/0287770 A1* | 11/2008 | Kurzweil | A61B 5/01 600/388 |
| 2012/0145633 A1* | 6/2012 | Polizzotti | C02F 1/36 210/708 |
| 2015/0342266 A1* | 12/2015 | Cooper | A41H 1/10 705/26.7 |
| 2016/0183602 A1* | 6/2016 | Rider | A61M 1/06 450/36 |
| 2018/0326130 A1* | 11/2018 | Thompson | A61M 1/06 |
| 2020/0100721 A1* | 4/2020 | Gozen | A61B 5/01 |
| 2022/0000385 A1* | 1/2022 | Elia | A61B 5/0536 |

* cited by examiner

*Primary Examiner* — Timothy K Trieu
(74) *Attorney, Agent, or Firm* — Law Offices of Kevin M. Jones & Associates LLC (57) ABSTRACT

A device and system for monitoring breast milk volume comprising a sensing module attached to a bra. The sensing module can include a processing unit configured to receive, store, and process readings measured by the sensing components of the module. The processing unit can be connected to a wireless transmitter that can be configured to transmit recorded and stored readings from the sensing module to a mobile device. The mobile device can display the transmitted data and further process the data to enable visualization of trends in the collected data.

18 Claims, 6 Drawing Sheets

APPARATUS AND METHOD OF USE TO MONITOR CHANGES IN BREAST MILK VOLUME

CROSS-REFERENCE TO RELATED APPLICATIONS

This application claims priority under 35 U.S.C. § 119(e) from U.S. Provisional Patent Application No. 63/1,477,404, by Haroon Iqbal Badat, "System, Method, and Apparatus to Monitor Breast Milk Volume" filed 9 Feb. 2021, which, by this statement, is incorporated herein by reference for all purposes.

BACKGROUND OF THE INNOVATION

Statement Regarding Federally Sponsored Research or Development

Not Applicable.

Reference to Sequence Listing, a Table, or a Computer Program Listing Compact Disc Appendix Not Applicable.

Field of the Innovation

The innovation relates generally to garments with electronically augmented functionality. More particularly, the innovation relates to a nursing bra with augmented functionality to monitor breast feeding of an infant.

Background of the Innovation

Current nursing bras are designed for nursing mothers to perform the basic intended functions for such clothing, providing physical support, while still allowing a mother/user/wearer relatively quick and easy access for infant feeding, breast pumping, etc. But current technology can significantly enhance nursing bra functionality to address concerns nursing mothers commonly face.

A prevalent concern of nursing mothers, especially new mothers, is adequate milk consumption by an infant during feeding. New infants are notorious for nipple latching issues which may result in little or no consumption of nourishment during what may have appeared as a successful feeding.

Other problems can persist throughout the nursing stage. For instance, once a child is comfortable in the feeding process, the soothing activity may lull them to sleep shortly after feeding is initiated. If a mother does not notice and awaken or encourage the feeding, nourishment received by the infant is hard to estimate. This may happen during the night, when the mother is also sleepy; or during the day, when a nursing mother may be distracted by other activities/surroundings.

Estimating the volume consumed during a feeding is important for monitoring the infant's nourishment, establishing healthy cycles/patterns for the infant, and helping a busy mother to adjust or plan future feedings amongst other of her life's activities.

A commonly employed method for estimating the volume of milk ingested by a baby while nursing involves weighing before and after feeding and converting the weight change into an estimate of the volume of milk ingested by the infant.

A new infant's weight is small enough to be measured with sufficient precision to determine differences from before to after feeding. But these measurements do not definitely determine ingested volume. The weight may be compromised by leakages, spit up, etc which may be in clothing and/or diapers.

With several feedings occurring in a single 24-hour period, and several taking place overnight, this process is time consuming and highly inconvenient. Additionally, as an infant continues to grow, the amount of each feeding becomes more indistinguishable from the baby's overall weight without increased precision of the scales used in the process.

Obviously, measurement of the mother's body weight is hardly precise enough to determine milk volume produced. But an alternative is to measure changes of isolated body parts. The primary issue becomes isolating the body part and measuring in a repeatable manner. Secondary issues are general convenience of the measuring process, accuracy, equipment, reliability, etc.

In U.S. Pat. No. 9,192,325, inventor Mardiks shows a bra designed to measure real-time changes in breast volume. The bra's sensing mechanism comprises a pressure sensor, an inflatable cuff that fits around the breast, and a pump to serve as an inflating mechanism. The bulkiness and power demands of the pump reduce the bra's practicality and portability.

Another measuring device is disclosed in patent No. KR 102051395 B1. The described device consists of a cup that is placed completely over the breast before and after each feeding to measure changes in breast volume.

The operation of this device presents the same shortcomings as the aforementioned method of weighing the baby before and after each feeding as it requires the user to manually take measurements. To measuring the volume consumed at each feeding, the device must be with the mother at all times. Further, the device's use requirements may be a significant inconvenience in many settings.

In U.S. Publication No. 2008/0077042 A1, Feldkamp discloses a bra fitted with conductivity sensors that can be placed on an infant's stomach to measure stomach fullness. While this approach varies from the previously described approaches on monitoring changes in breast volume directly, it requires additional equipment and effort as compared to a traditional nursing bra operated in its normal manner.

There is a need for a measuring method that is portable, usable, and easily incorporated into a nursing mother's routine without additional bulky equipment or intrusive complicated requirements which can intrude into this mother/infant bonding activity.

DETAILED DESCRIPTION OF THE PREFERRED EMBODIMENTS

The innovation is electronic augmentations that enhance a nursing bra to measure changes in breast weight for purposes of breast milk volume monitoring. A mobile computing device may be used to provide further monitoring capability and a convenient user interface for immediate interaction with the augmentations.

Augmentations comprise integrating a battery powered electronic controller into a nursing bra. The controller is connected to one or more sensing modules integrated into various areas of the nursing bra according to the sensor. The bra's band fastener, and cup clasp are electronically conductive or include integrated connection points to provide 'switch like' operations through normal bra usage.

The battery may be inductively recharged or may incorporate a charging port to maintain the battery between uses preventing the need to change out batteries, or otherwise power the electronics. By using an electronically conductive fastener as a power switch, the controller becomes functional when worn by the user and automatically turn off when removed from the body. Similarly, the act of opening or closing a bra cup's clasp indicates possible feeding activities without any direct user interaction with the controller.

In the preferred embodiment, the controller periodically interprets sensing elements to determine the breast volume. Opening a bra cup's clasp to access the mother's breast is an indication of possible feeding activities commencing. Closing the clasp is an indication the feeding activities have finished. The controller may read the sensing element when feeding activities are completed and compare it to periodic readings before feeding activities commenced to determine the volume of milk produced during the feeding.

Initial calibration involves taking a measurement, expressing a set amount of breast milk, then taking another measurement to produce a functional data point. Continuing the process produces more data points, forming a calibration curve from which a functional relation can be established.

In the preferred embodiment, sensing elements determine the weight of the breast and presume a linear correlation, though not necessarily a direct correlation since the electrical characteristic being measured is not the actual weight.

The primary sensing elements of the preferred embodiment measure the stress a breast in a bra cup places on the shoulder strap of the bra. The sensing elements produce a representative electrical signal. To increase reliability, a running average may be maintained across multiple measurements.

In another embodiment, secondary sensors may be incorporated and utilized to produce one or more complex calibration curves. In other embodiments, additional sensors may be utilized to filter data from the primary sensing elements.

For example, use of a tilt sensor can determine measurements taken in standing, sitting, lying positions. Use of an accelerometer may be used to differentiate resting, walking, running, etc measurements.

Differentiated measurements may be used to discard select measurements, or to sort measurements into categories with different calibration curves for each category. Calibration curves for different categories can also be inter-related through intersecting data points.

Calibration functions can be verified and/or adjusted by comparing determined measurements against known volumes of milk expressed by breast pumping. Adjusted calibrations may be used to modify previously logged data at the discretion of the user.

Measurements and other data are collected by an electronic controller integrated into the bra. Sensing elements may be incorporated into the electronic controller or may be external to the controller. In one embodiment the controller communicates with a mobile computing device to provide additional processing and/or long-term storage, as well as a convenient user interface.

In another embodiment the electronic controller may store data internally and communicate with a separate computing device periodically. In the preferred embodiment, the separate computing device is a smart phone. One skilled in the arts would appreciate that other computing devices may include, but is not limited to smart watches, tablets, laptops, or desktop computing devices.

The communication between the controller and the mobile computing device may be wired or wireless. A wireless Bluetooth™ communication is desired for the preferred embodiment presented herein. The mobile device receives data from the controller and logs the timestamp and volume of breast milk for each feeding.

Another embodiment may log the volume from a feeding as separate volumes produced from the left and right breast. In another embodiment, volume data may be supplemented with a name/label for tracking of multiple babies for situations where more than one child is currently feeding from the same mother e.g., after multiple births.

During regular operation, the controller continuously takes measurements at periodic intervals, collecting data internally. It may be configured to go into a sleep state and/or power down components between the periodic measurements to conserve power. The electronic controller can further by only activating wireless communication during feeding activities. This is accomplished by detecting changes in the state of either bra cup's clasp.

When a signal is received on the opening of a bra cup's clasp, indicating feeding activity has commenced, the electronic controller determines the most recent measurement for the breast, and waits for the clasp to be closed. On receiving a closing clasp signal, the controller takes another measurement of the breast, determines the milk volume, connects to the computing device, and transmits the feeding data.

The innovation has several advantages including the ability to monitor breast milk volume without bulky equipment, a continuous record of feedings, a user-friendly experience requiring few changes from traditional nursing bras allowing the bra to be integrated into a daily routine with little intrusion into the mother/infant bonding time. The embodiment presented is one possible configuration and others which are in accordance with the teachings herein will be apparent to one skilled in the arts.

DETAILED DESCRIPTION OF THE DRAWINGS

Figure 1:
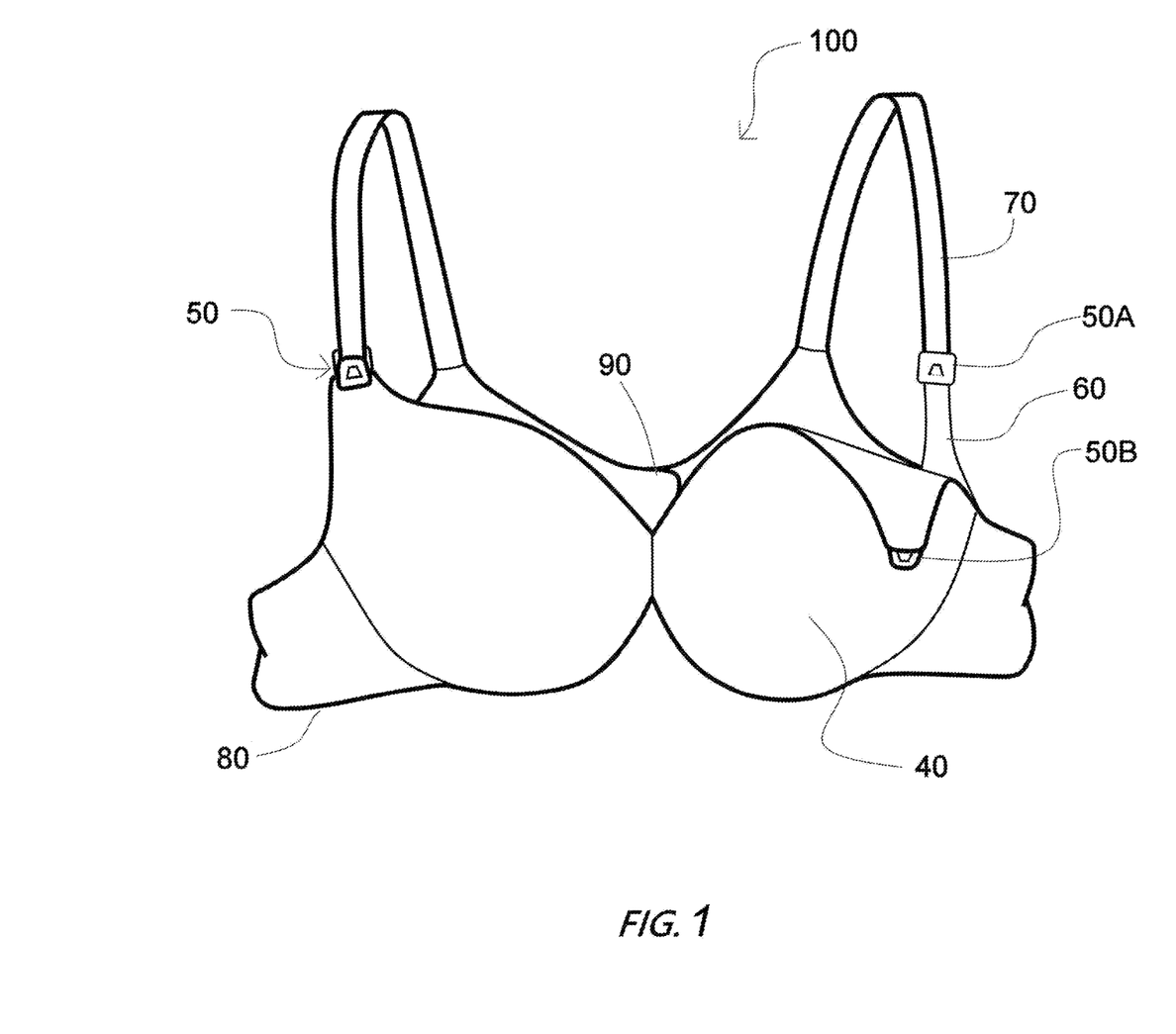
FIG. 1 is an example of a nursing bra illustrating drop down cups and a side sling inner layer to be augmented for monitoring breast milk volume in accordance with an exemplary implementation of the present innovation.

FIG. 1 is an example of a nursing bra illustrating drop down cups and a side sling inner layer to be augmented for monitoring breast milk volume in accordance with an exemplary implementation of the present innovation. A nursing bra 100 is described here to clarify descriptive terms for various elements and assist understanding of the teaching presented.

A nursing bra 100 has drop down cups 40 with clasps 50 to provide access for feedings. The cups 40 of a nursing bra 100 have an inner layer, A-frame (not illustrated) or side sling 60, to retain the shoulder strap 70 when the clasp hook 50B is released from the clasp base 50A. A band 80 is joined by a fastener 90 between the straps 70 in the back, or between the cups 40 in the front.

Figure 2A:
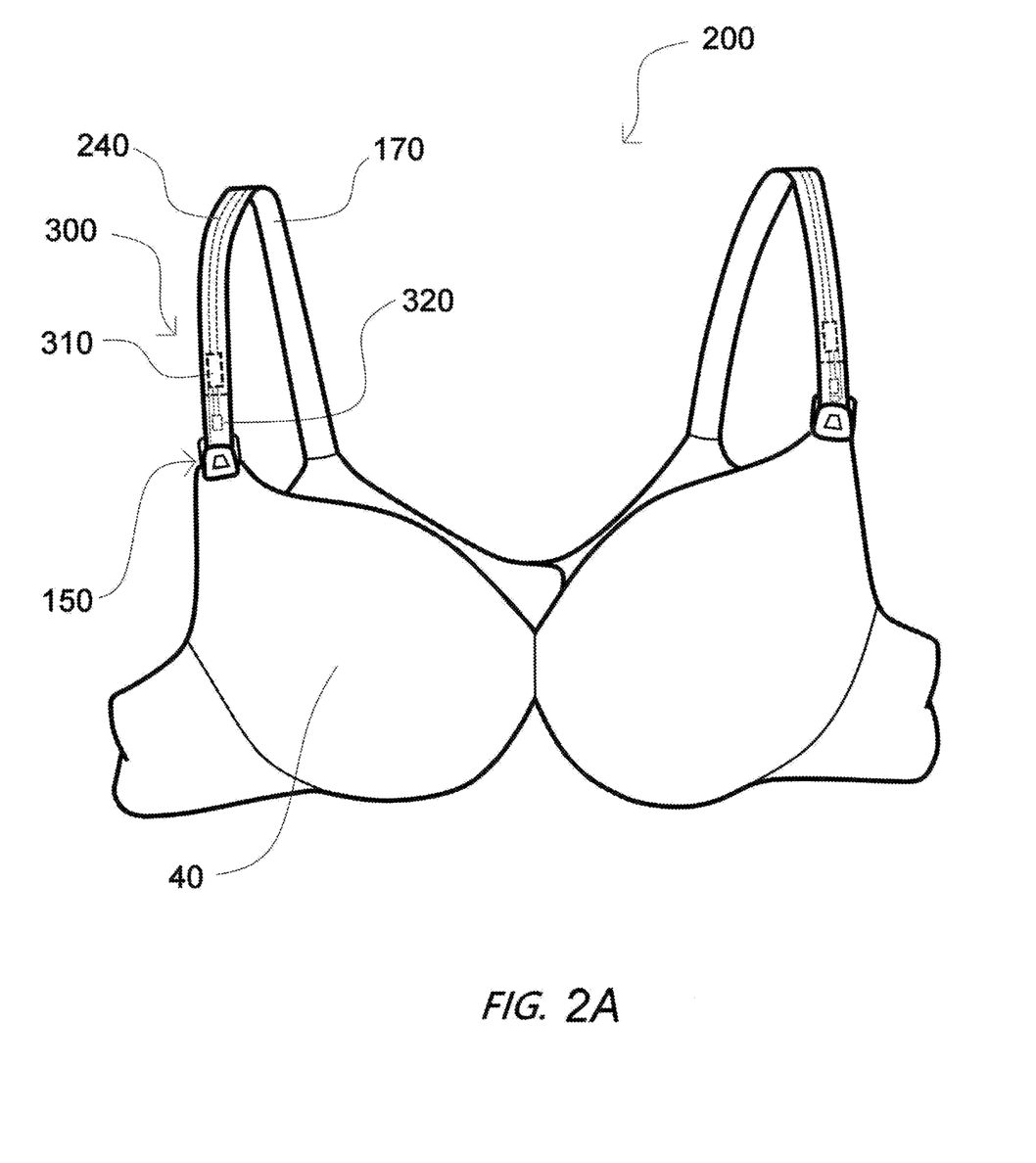
FIGS. 2A and 2B are front and rear views of a nursing bra augmented in accordance with an exemplary implementation of the innovation.
Figure 2B:
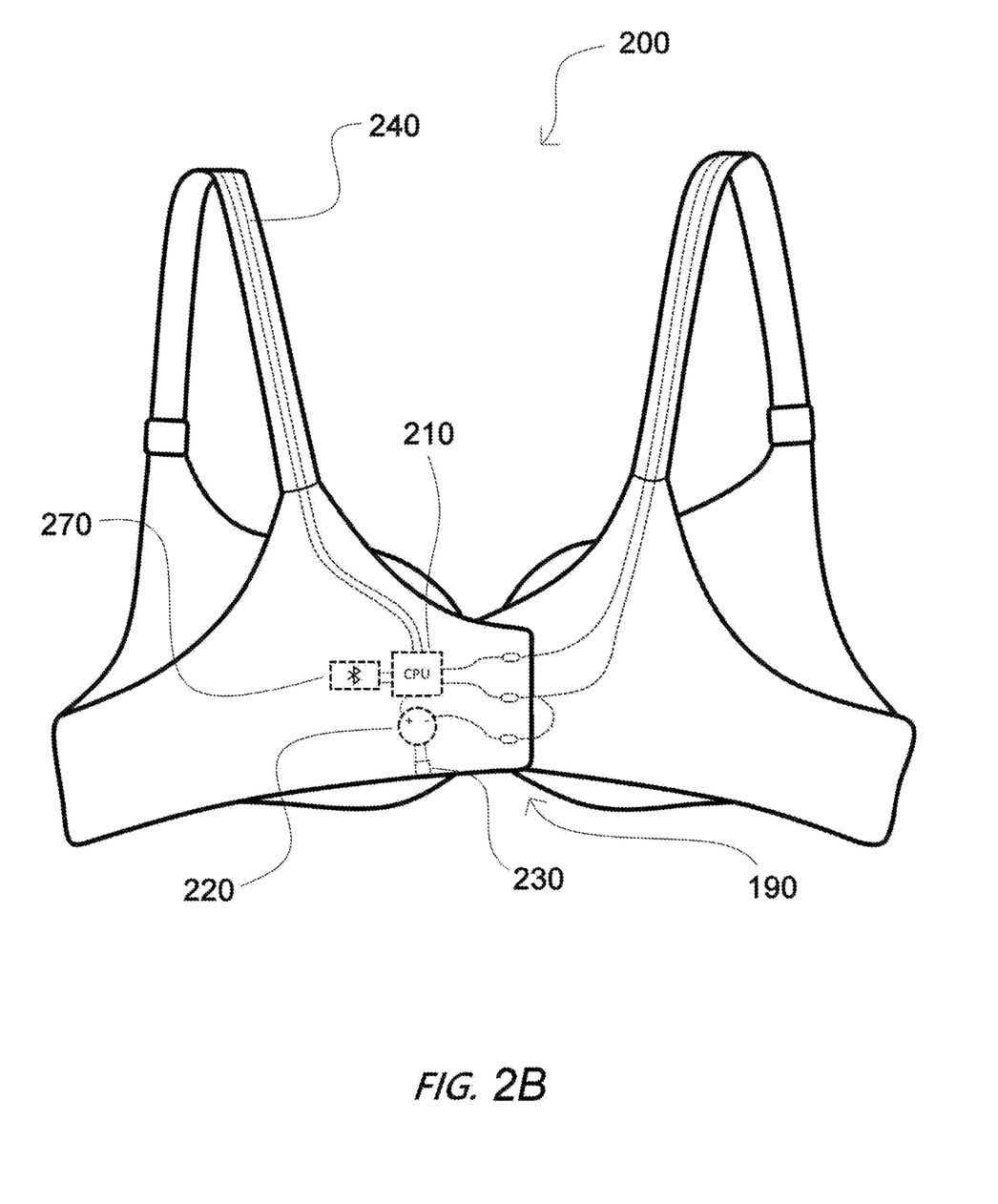

FIGS. 2A and 2B are front and rear views of an augmented nursing bra in accordance with an exemplary implementation of the innovation. The augmented nursing bra 200 requires the cup clasp 50 and the fastener 90 utilize electrically conductive versions. This allows the opening and closing of the clasp 150 or fasteners 190 to provide a "switch-like" signal by simply opening or closing the clasp hook 150B and clasp base 150A or the fastener hook 190A and fastener eye 190B. Other methods are obvious to those skilled in the arts. The goal is for normal operation of a nursing bra's elements to assist augmented functionality without additional steps when possible.

The sensing module 300 illustrated is duplicated on each cup 40. The sensing module 300 in this embodiment is a strain gauge 320 bonded to the material of the shoulder strap 170 and connected to any needed support circuitry 310. One skilled in the arts would appreciate that any support circuitry is dependent on the sensor requirements and may be separate or integrated into the sensor or other elements, such as being a part of the bra clasp 150.

In this embodiment the controller 210 is in the back of the bra 200 within the band 180 (not indicated). Placement in the band 180 allows elastic and padding to secure and support the controller 210, battery 220, communications element 270 and charging port 230 or inductive charging loop.

One sensing module 300 is connected to the electronic controller 210 by conductive wires 240 integrated into the material of the shoulder strap 170. In this embodiment, the hook and eye fastener 190 electrically conduct communication signals between the controller 210 and the other sensing module 300 on the opposite side of the body.

In another embodiment, communication signals may be routed through the cups 40 rather than crossing the fastener 190. In either embodiment, the hook and eye fastener 190 may still be used to complete connection between the battery 220 and the controller 210, providing a convenient power switching functionality.

Figure 3:
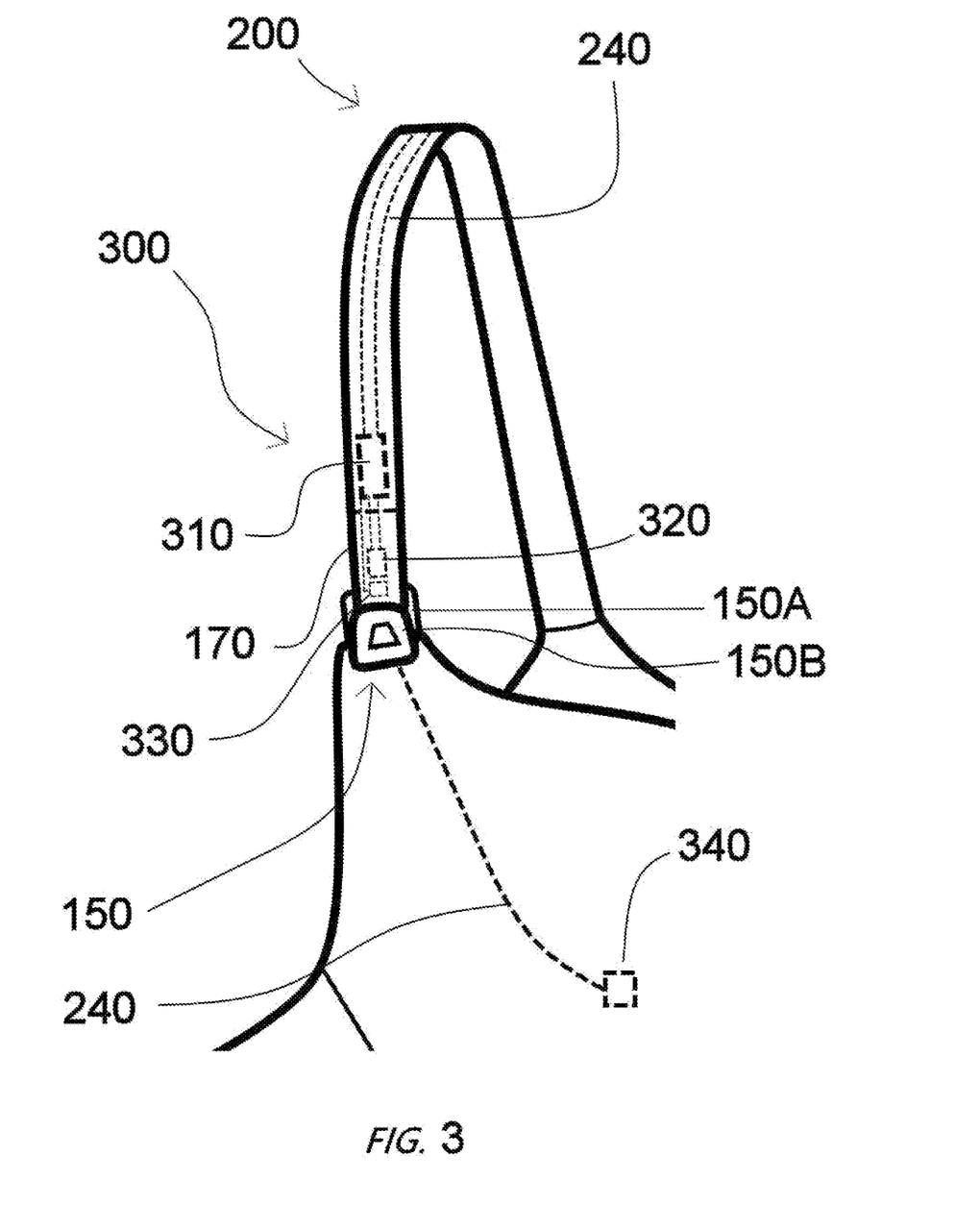
FIG. 3 is a close-up view of a sensing module from FIG. 2 enhanced with secondary sensors in accordance with an exemplary implementation of the innovation.

FIG. 3 is a close-up view of a sensing module from FIG. 2 enhanced with secondary sensors in accordance with an exemplary implementation of the innovation. The primary sensor, the strain gauge 320, from the sensing module 300 in FIG. 2 is enhanced with a tilt sensor 330 and an accelerometer 340, all of which is connected to supporting circuitry 310.

In this embodiment secondary sensors 330 and 340 are utilized for filtering measurements from the primary sensor 320. I.e., the periodic measurements are only stored if the tilt sensor 330 indicates the wearer, the mother, is in a particular position (e.g., upright) and the accelerometer 340 detects little to no motion of the breast at the time the measurement is taken.

Input from the tilt sensor 330 and accelerometer 340 in unison enable the sensing module 300 to reduce errors stemming from inconsistent orientation between measurements and/or excessive motion. Additionally, input from the tilt sensor 330 and the accelerometer 340 can be used for algorithmic correction of the values measured from the strain gauge 320.

After a feeding is completed and the clasp 150 is in the attached position (as shown in FIG. 2A), the system, governed by input from the tilt sensor 330 and the accelerometer 340 to ensure that wearer is in a preferred orientation and motionless when values from the strain gauge 320 are recorded, can begin recording values from the sensing module 300.

The recorded values are converted from voltage to volume of milk using calibration formulas. The stored measurement data is then transferred to a mobile computing device 300 via Bluetooth™ or another means of (preferably wireless) data transmission for visualization and tracking of the collected data.

Figure 4:
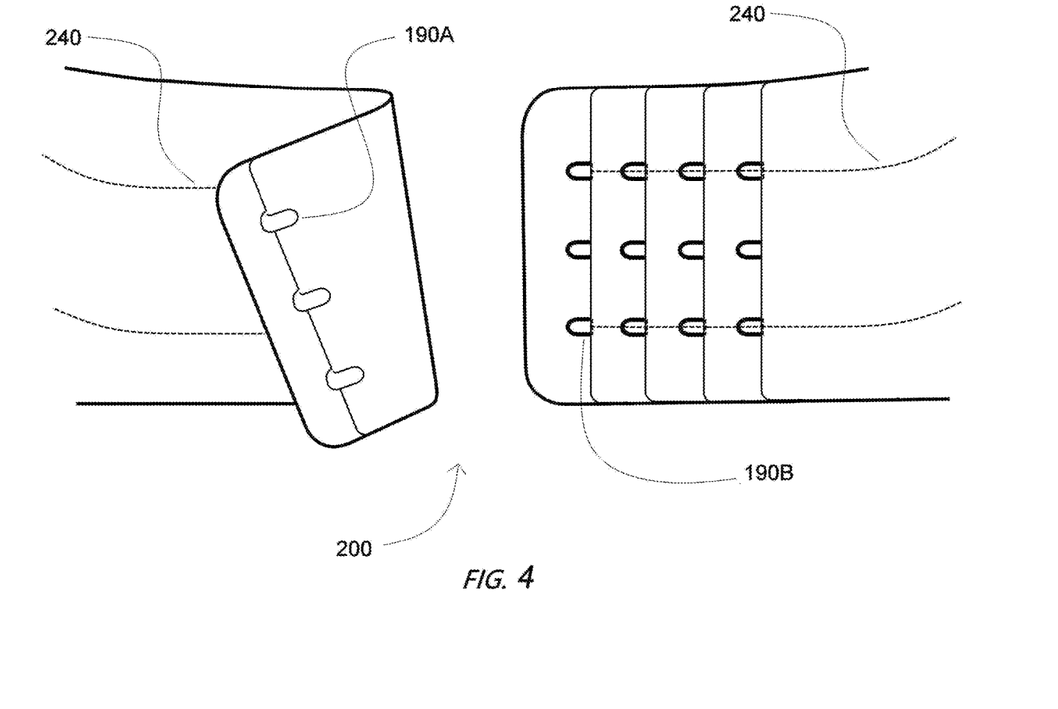
FIG. 4 is a view of the bra fasteners with electrical connection to the multiple clasp

FIG. 4 is a view of the bra fastener with electrical connection to the multiple clasps. FIG. 4 depicts the bra closure, or fastener 190. The hooks 190A of the fastener 190 latch on to the loops 190B to secure the bra 200 around the wearer. Both the hooks 190A and the loops 190B are conductive and form a closed circuit when in the closed position.

A wire 240 integrated into the bra's 200 fabric material connects the rechargeable battery 220 and processing unit (electronic controller 210) to the hooks 190A of the fastener 190. Another wire connected to the loops 190B of the bra closure 190 connects the sensing module 300 on the opposite side of the bra with the rechargeable battery 220 and electronic controller 210.

Figure 5:
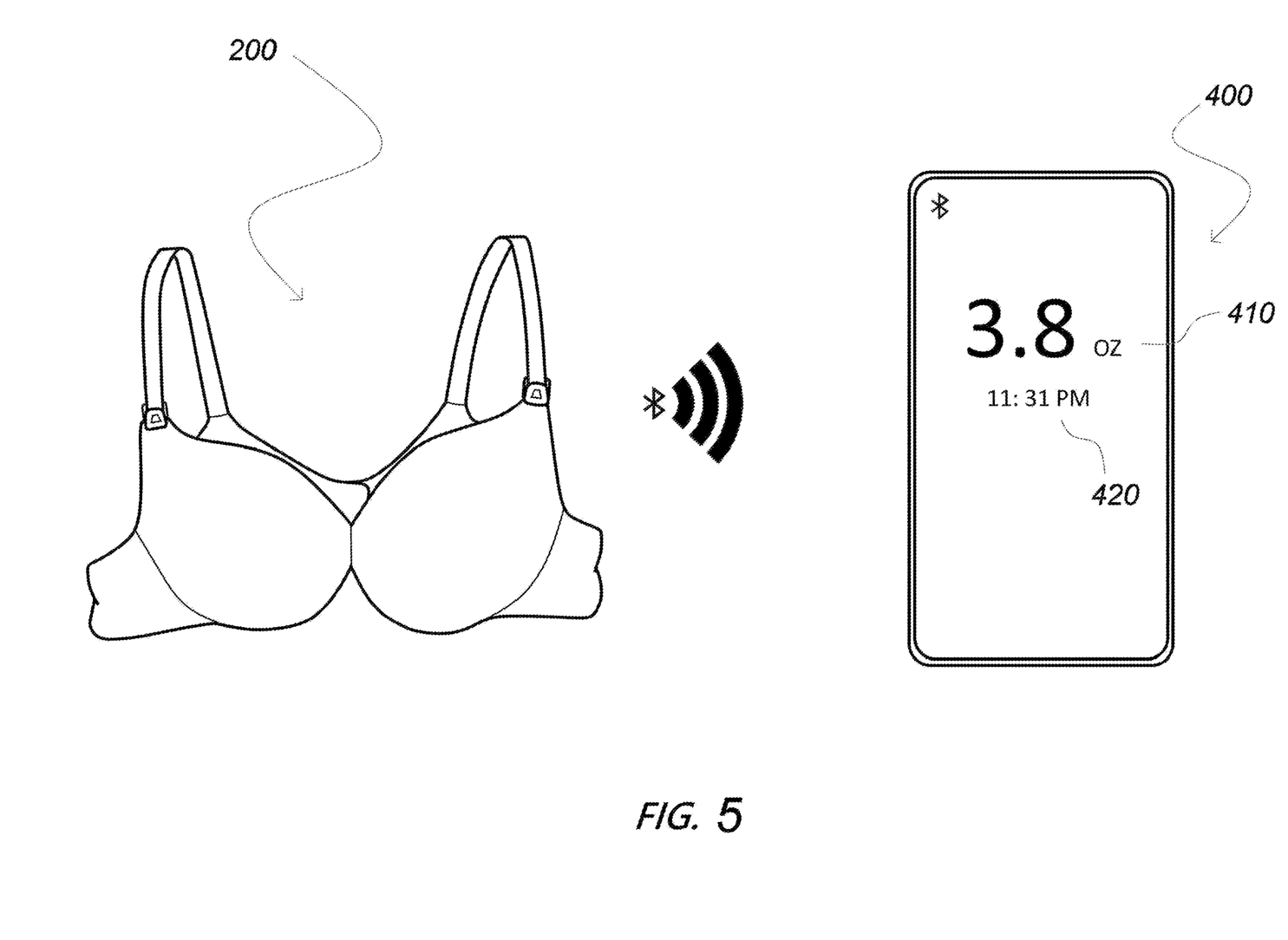
FIG. 5 is a diagram of a system for monitoring breast milk volume in accordance with an exemplary implementation of the present innovation.

FIG. 5 depicts a diagram of a system for monitoring breast milk volume in accordance with an exemplary implementation of the present innovation. Specifically, FIG. 5 depicts the augmented bra 200 in communication 270' with a mobile computing device 400. The computing device is configured to accept, display, and log data from feedings consisting at least of the feeding time 420 and the breast milk volume 410 determined from the measurements by the calibration curve.

The diagrams in accordance with exemplary embodiments of the present innovation are provided as examples and should not be construed to limit other embodiments within the scope of the innovation. For instance, materials, placements, orientations, and/or styles should not be construed to limit the innovation to the specific selections illustrated. Elements, specific devices, formats, may vary in detail. Specific information should be interpreted as illustrative for discussing exemplary embodiments and not as limiting to the innovation.

The above discussion is meant to be illustrative of the principles and various embodiments of the present innovation. Numerous variations and modifications will become apparent to those skilled in the art once the above disclosure is fully appreciated. It is intended that the following claims be interpreted to embrace all such variations and modifications.

What is claimed:

1. An augmented nursing bra, the augmented nursing bra comprising: one or more electronic weight sensors configured to measure forces applied to shoulder straps by the weight of breast in bra cups of the augmented nursing bra; an electronically conductive bra cup clasp, producing electronic signals upon opening or closing of the bra cup clasp of a bra cup; an electronic controller with supporting circuitry; and a power source.

2. The nursing bra as defined in claim 1, further comprising an electronically conductive bra band fastener, wherein the power source is connected to the electronic controller and support circuitry when the band fastener is fastened and disconnected when the band fastener is unfastened.

3. The nursing bra as defined in claim 1, wherein the power source is one or more batteries.

4. The nursing bra as defined in claim 3, wherein the batteries are rechargeable.

5. The nursing bra as defined in claim 4, wherein the power source further comprises a charging port.

6. The nursing bra as defined in claim 4, wherein the power source further comprises an inductive charging loop for inductively recharging the batteries.

7. The nursing bra as defined in claim 1, wherein the supporting circuitry further comprises: a communications unit.

8. The nursing bra as defined in claim 7, wherein the communications unit is a wireless communication unit.

9. The nursing bra as defined in claim 8, wherein the wireless communication unit is a Bluetooth® device.

10. The nursing bra as defined in claim 1, wherein the supporting circuitry further comprises a tilt sensor for detecting orientation of a wearer.

11. The nursing bra as defined in claim 1, wherein the supporting circuitry further comprises an accelerometer for detecting movement of a wearer.

12. A method of monitoring changes in breast milk volume comprising:
utilizing an augmented nursing bra worn by a wearer, the augmented nursing bra comprising: one or more electronic weight sensors configured to measure forces applied to shoulder straps by the weight of breasts in bra cups of the nursing bra, electronically conductive bra cup clasps, producing electronic signals upon opening or closing of the bra cup clasps of the bra cups, an electronic controller with supporting circuitry, and a power source; recording the measure of forces applied to each shoulder strap; determining a change in breast milk volume by analyzing changes in the recorded measure of forces applied to the shoulder strap by a feeding activity occurring between opening and closing of the bra cup clasps.

13. The method as defined in claim 12 wherein the feeding activity comprises nursing, pumping, or manually expressing milk from one or more breasts.

14. The method as defined in claim 12 wherein the controller is configured to periodically record the measure of forces applied to the shoulder strap, and determining the change in breast milk volume comprises:
upon opening a bra clasp, selecting a first measurement from recent measurements recorded by the controller for the shoulder strap that corresponds with the bra clasp opened; waiting for the closing signal of the same bra clasp;
recording a second measurement for the shoulder strap that corresponds with the bra clasp; calculating a change between the second and first measurements; and determining a volume of the breast milk represented by the change in the first and second measurements by applying a calibration curve function.

15. The method as defined in claim 12 wherein the electronic controller supporting circuitry further comprises a communications unit;
the electronic controller is configured to periodically record the measure of forces applied to the shoulder strap; and determining the change in breast milk volume comprises: upon opening a bra clasp, selecting a first measurement from recent measurements recorded by the controller for the shoulder strap that corresponds with the bra clasp opened; waiting for the closing signal of the same bra clasp; recording a second measurement for the shoulder strap corresponding with the bra clasp; and transmitting the recorded data to a computing device for analysis of volume represented by the change in the first and second measurements.

16. The method as defined in claim 15 further wherein the computing device is configured to receive, display, and log the transmitted data.

17. The method as defined in claim 15 further wherein the computing device is configured to query a user for additional information comprising one or more of the following:
activity type comprising: feeding, manual expressing, pumping, or leaking;
other activity identifiers comprising: infant name, purpose; and/or
the volume expressed.

18. The method as defined in claim 17 wherein the computing device is configured to recalibrate a calibration curve after pumping activity of a known volume.

* * * * *